US006652506B2

(12) United States Patent
Bowe et al.

(10) Patent No.: US 6,652,506 B2
(45) Date of Patent: Nov. 25, 2003

(54) SELF-LOCKING HANDLE FOR STEERING A SINGLE OR MULTIPLE-PROFILE CATHETER

(75) Inventors: Wade A. Bowe, Temecula, CA (US); Jesse Flores, Perris, CA (US); Andrea M. Moore, Murrieta, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 315 days.

(21) Appl. No.: 09/849,189

(22) Filed: May 4, 2001

(65) Prior Publication Data

US 2002/0165484 A1 Nov. 7, 2002

(51) Int. Cl.[7] .............................................. A61M 25/00
(52) U.S. Cl. ..................... 604/523; 600/585; 604/528
(58) Field of Search ................................ 604/523, 528, 604/95.07, 525; 600/585

(56) References Cited

U.S. PATENT DOCUMENTS

| | | | |
|---|---|---|---|
| 3,071,161 A | 1/1963 | Ulrich | |
| 3,253,524 A | 5/1966 | Ashizawa et al. | |
| 3,897,775 A | 8/1975 | Furihata | |
| 4,586,923 A | 5/1986 | Gould et al. | |
| 4,921,482 A | 5/1990 | Hammerslag et al. | |
| 4,998,916 A | 3/1991 | Hammerslag et al. | |
| 5,037,391 A | 8/1991 | Hammerslag et al. | |
| 5,108,368 A | 4/1992 | Hammerslag et al. | |
| 5,190,050 A | * 3/1993 | Nitzsche | 600/585 |
| 5,195,968 A | 3/1993 | Lundquist et al. | |
| 5,199,950 A | 4/1993 | Schmitt et al. | |
| 5,228,441 A | 7/1993 | Lundquist | |
| 5,254,088 A | 10/1993 | Lundquist et al. | |
| 5,273,535 A | 12/1993 | Edwards et al. | |
| 5,275,151 A | 1/1994 | Shockey et al. | |
| 5,299,562 A | 4/1994 | Heckele et al. | |
| 5,315,996 A | 5/1994 | Lundquist | |
| 5,318,525 A | 6/1994 | West et al. | |
| 5,318,526 A | 6/1994 | Cohen | |
| 5,322,064 A | 6/1994 | Lundquist | |
| 5,327,905 A | 7/1994 | Avitall | |
| 5,329,923 A | 7/1994 | Lundquist | |

(List continued on next page.)

FOREIGN PATENT DOCUMENTS

EP   1 046 406 A   10/2000
WO   WO 94 11057 A   5/1994

OTHER PUBLICATIONS

Grafton A. Smith, M.D. and Edwin L. Brackney, M.D., "Preliminary Report on a New Method of Intestinal Intubation with the Aid of a Flexible Stylet with Controllable Tip," Dept. of Surgery, University of Minnesota Medical School, vol. 27, #6, Jun. 1950, pp. 817–821.

*Primary Examiner*—Thor Campbell
(74) *Attorney, Agent, or Firm*—Fulwider Patton Lee & Utecht, LLP

(57) ABSTRACT

A catheter handle includes a steering controller with a self-locking mechanism to be used in conjunction with a steerable catheter shaft. A compression spring portion of the self-locking mechanism is located between the steering controller and a handle shell and causes alternating protrusions and recesses on the steering controller and on the handle shell to engage, thus locking the steering controller into a fixed position with the handle shell. Through a single-handed operation, an operator enables steering controller rotation by applying a force to the steering controller, which disengages the steering controller from the handle shell. The operator then adjusts the profile of a distal-end region of the catheter by rotating the steering controller. When the desired profile of the distal-end region of the catheter has been obtained, the operator removes the force from the steering controller and the spring decompresses to reengage the steering controller with the handle shell.

28 Claims, 4 Drawing Sheets

U.S. PATENT DOCUMENTS

| | | | |
|---|---|---|---|
| 5,334,145 A | 8/1994 | Lundquist et al. | |
| 5,336,182 A | 8/1994 | Lundquist et al. | |
| 5,358,478 A | 10/1994 | Thompson et al. | |
| 5,363,861 A | 11/1994 | Edwards et al. | |
| 5,364,351 A | 11/1994 | Heinzelman et al. | |
| 5,383,852 A | 1/1995 | Stevens-Wright | |
| 5,383,923 A | 1/1995 | Webster, Jr. | |
| 5,395,327 A | 3/1995 | Lundquist et al. | |
| 5,456,664 A | 10/1995 | Heinzelman et al. | |
| 5,471,982 A | 12/1995 | Edwards et al. | |
| 5,478,330 A | 12/1995 | Imran et al. | |
| 5,507,725 A | 4/1996 | Savage et al. | |
| 5,512,035 A | 4/1996 | Konstorum et al. | |
| 5,531,686 A | 7/1996 | Lundquist et al. | |
| 5,545,200 A | 8/1996 | West et al. | |
| 5,642,736 A | 7/1997 | Avitall | |
| 5,666,970 A * | 9/1997 | Smith | 600/585 |
| 5,687,723 A | 11/1997 | Avitall | |
| 5,728,144 A | 3/1998 | Edwards et al. | |
| 5,730,704 A | 3/1998 | Avitall | |
| 5,755,760 A | 5/1998 | Maguire et al. | |
| 5,810,802 A | 9/1998 | Panescu et al. | |
| 5,820,591 A | 10/1998 | Thompson et al. | |
| 5,855,552 A | 1/1999 | Houser et al. | |
| 5,860,953 A | 1/1999 | Snoke et al. | |
| 5,865,800 A | 2/1999 | Mirarchi et al. | |
| 5,891,088 A | 4/1999 | Thompson et al. | |
| 5,893,885 A | 4/1999 | Webster, Jr. | |
| 5,916,147 A | 6/1999 | Boury | |
| 5,984,907 A | 11/1999 | McGee et al. | |
| 5,987,344 A | 11/1999 | West | |
| 6,007,531 A | 12/1999 | Snoke et al. | |
| 6,017,322 A | 1/2000 | Snoke et al. | |
| 6,022,343 A | 2/2000 | Johnson et al. | |
| 6,027,473 A | 2/2000 | Ponzi | |
| 6,030,360 A * | 2/2000 | Biggs | 604/95.01 |
| 6,033,378 A | 3/2000 | Lundquist et al. | |
| 6,042,562 A | 3/2000 | Amor | |
| 6,063,077 A | 5/2000 | Schaer | |
| 6,132,390 A | 10/2000 | Cookston et al. | |
| 6,142,994 A | 11/2000 | Swanson et al. | |
| 6,163,716 A | 12/2000 | Edwards et al. | |
| 6,208,881 B1 | 3/2001 | Champeau | |
| 6,511,471 B2 * | 1/2003 | Rosenman et al. | 604/528 |
| 6,522,933 B2 * | 2/2003 | Nguyen | 607/116 |

* cited by examiner

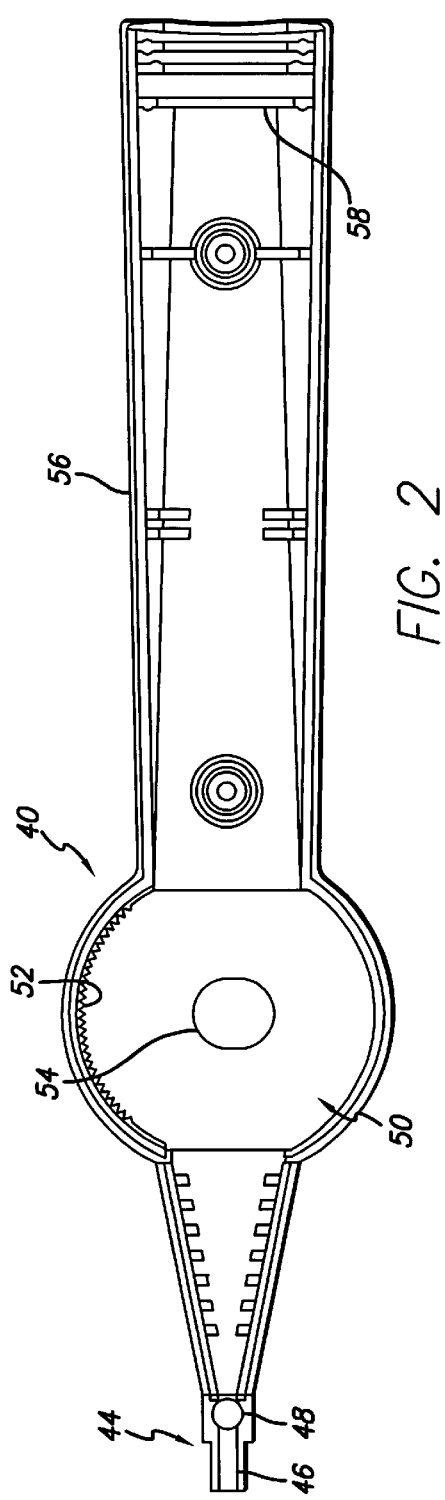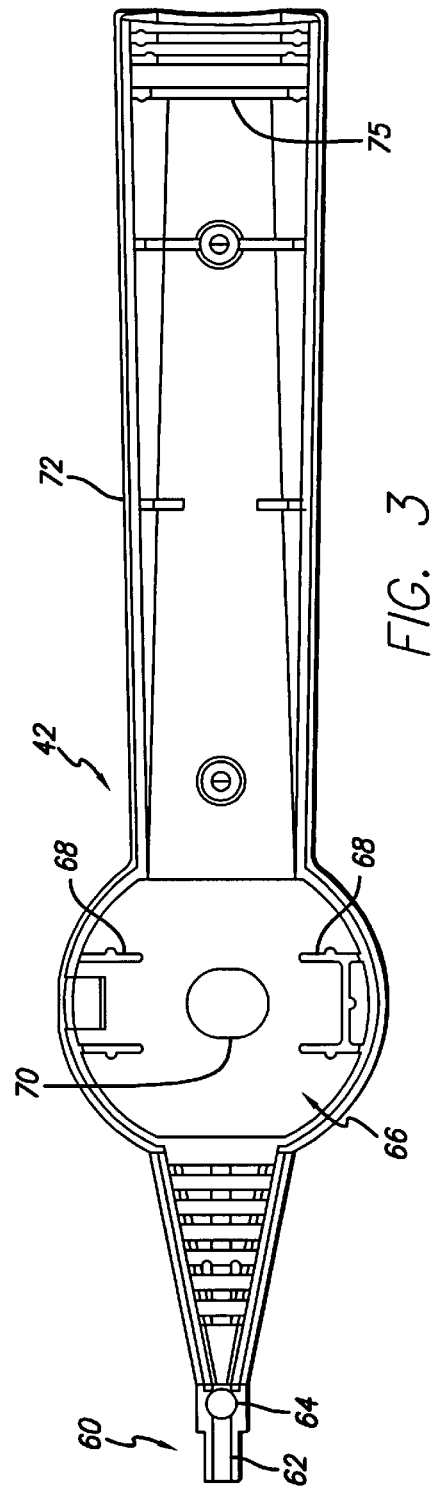

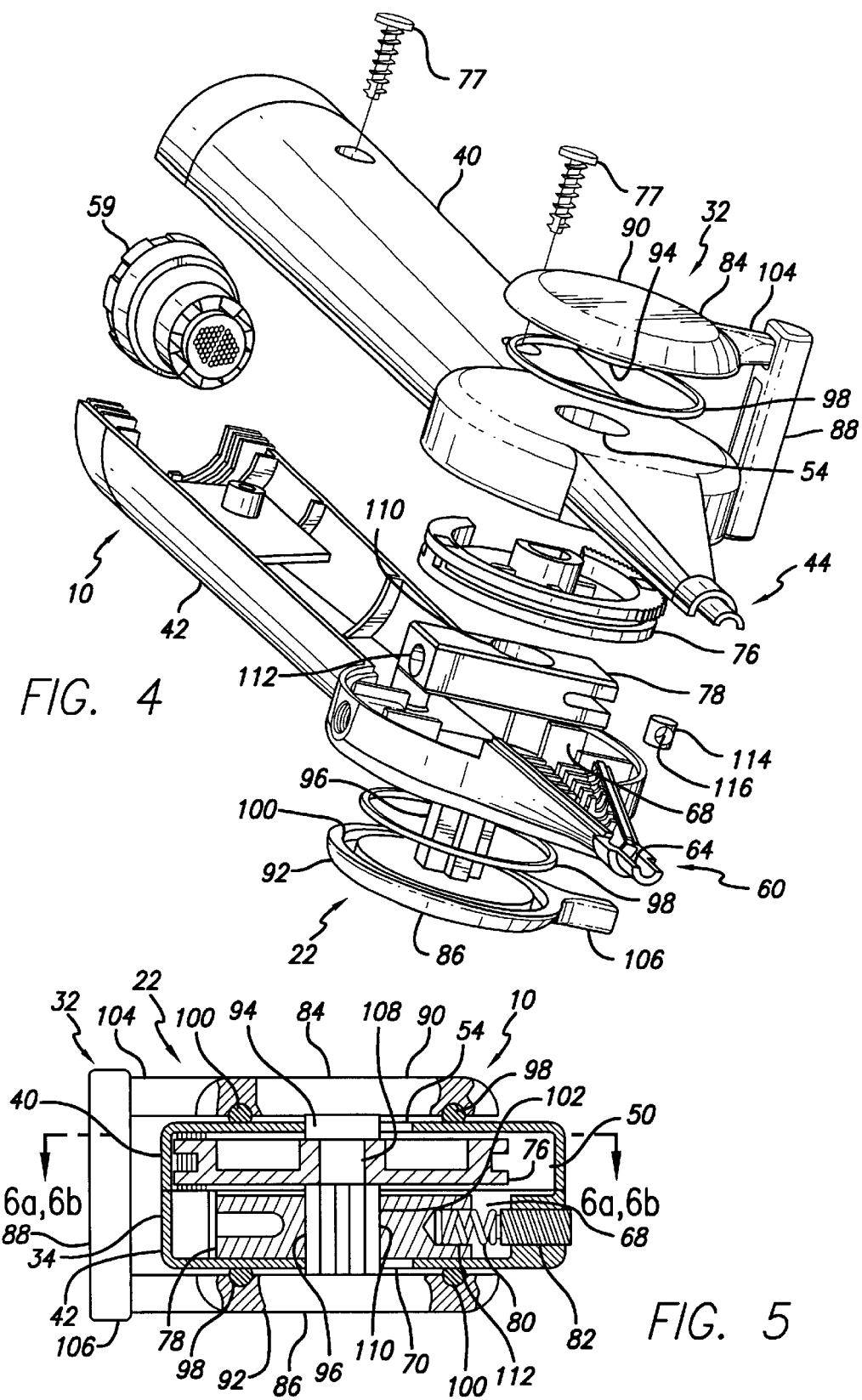

SELF-LOCKING HANDLE FOR STEERING A SINGLE OR MULTIPLE-PROFILE CATHETER

BACKGROUND OF THE INVENTION

The invention relates generally to steerable catheters, and more particularly to a steerable catheter having a handle with a steering controller that has a self-locking mechanism that allows the catheter profile to be changed and locked in place through the single-handed manipulation of the steering controller.

In many medical procedures, it is necessary to place a catheter at a particular location within the patient's body. Precise placement of the catheter is more easily accomplished when a steerable catheter is used. Such catheters are typically flexible at the distal end, and the profile at the distal end is adjustable.

Changing the profile of the distal-end region of a steerable catheter typically involves the use of a steering tendon that is housed within the catheter shaft. The steering tendon is usually a wire that has its distal end attached to the distal-end region of the catheter shaft. The proximal end of the catheter shaft attaches to a handle. The proximal end of the steering tendon exits through the proximal end of the catheter shaft and attaches to a steering controller within the handle.

The profile of the distal-end region of the catheter shaft can be adjusted from its non-steered configuration by manipulating the steering controller from a neutral position so that the steering tendon is axially displaced in the proximal direction. Axially displacing the steering tendon in the proximal direction places the steering tendon in tension. Placing the steering tendon in tension, in turn, causes the catheter shaft to compress preferentially on the side where the steering tendon is attached. This causes a deflection of the distal-end region. If the steering controller is released, the distal-end region of the catheter shaft typically springs back to its natural state due to the structure of the catheter shaft, thus moving the steering tendon and the steering controller back to their neutral positions.

It is often necessary to maintain the force exerted on the steering tendon during the course of a medical procedure so as to retain the deflected profile of the distal-end region of the catheter. In some of the existing steerable catheters, maintaining the force exerted on the steering tendon requires the operator to manually hold the steering controller in place. However, it is often difficult for the operator to maintain a constant amount of force on the steering tendon for an extended period of time or while further manipulating the handle.

In other existing steerable catheters, an additional knob attached to the steering controller is used to lock the displacement of the steering tendon at its present position. This knob is used to tighten the steering controller against a friction plate within the handle housing until the resulting friction is sufficient to prevent the steering controller from moving from its present position. Typically, the operator must turn this knob with one hand while the other hand is used to maintain the preferred position of the steering controller relative to the handle housing. Thus, locking the steering controller in other steerable catheters is a two-handed operation.

Hence, those skilled in the art have identified a need for an improved catheter handle, and one with a steering controller that can be manipulated to a new position and locked in place through a single-handed operation. The present invention fulfills these needs and others.

SUMMARY OF THE INVENTION

Briefly, and in general terms, the present invention is directed to a catheter handle with a steering controller that includes a self-locking mechanism to be used in steering a single or multiple-profile catheter. The steering controller can be manipulated to establish a new profile of the catheter and locked in place with the self-locking mechanism through a single-handed operation.

In a first aspect, the invention relates to a handle for steering a catheter shaft that has a proximal region and a distal-end region and at least one steering tendon. The steering tendon has a distal end attached to the shaft distal-end region and a proximal end that exits the proximal end of the shaft. The handle includes a shell housing that is attached to the proximal end of the catheter shaft. The handle also includes a steering controller that is carried by the shell housing and has the proximal end of the at least one steering tendon connected thereto. The steering controller is adapted for movement to apply tension to the at least one steering tendon. Further included in the handle are a means for retaining the steering controller in a locked position to prevent the steering controller from moving, and means for moving the steering controller from the locked position to a free position wherein the steering controller is manipulable to adjust tension to the least one steering tendon.

In a detailed aspect of the invention, the steering controller includes a rotatable steering knob that includes a shaft portion located internal the shell housing and a controller portion located external the shell housing. The steering controller also includes a rotatable steering disk located internal the shell housing and attached to the shaft portion of the knob. In another detailed aspect, the retaining means includes first mating means that are carried by the shell housing, second mating means that are carried by the steering controller, and means for biasing the second mating means against the first mating means such that the first and second mating means engage. In a more detailed aspect, the first mating means and the second mating means each comprise a plurality of alternating protrusions and recesses. In a further detailed aspect, the plurality of alternating protrusions and recesses form teeth. In another detailed facet, the handle further includes means for adjusting the force with which the biasing means biases the second mating means against the first mating means. In a more detailed facet, the adjusting means includes a screw. In a further detailed facet, the biasing means includes any one of a compression spring, tension spring, leaf spring and Belleville spring washers. In another detailed facet, the means for moving the steering controller includes means for receiving force sufficient to disengage the second mating means from the first mating means. In a further detailed facet, the steering controller includes a rotatable steering knob that has a shaft portion located internal the shell housing and a controller portion located external the shell housing, and the force-receiving means include the controller portion.

In a second aspect, the invention relates to a handle for steering a catheter shaft that has a proximal region and a distal-end region and at least one steering tendon. Each steering tendon has a distal end attached to the shaft distal-end region and a proximal end that exits the proximal end of the shaft. The handle includes a shell housing that is attached to the proximal end of the catheter shaft and has a plurality of alternating protrusions and recesses positioned within the shell housing. The handle also includes a steering controller that is carried by the shell housing and has a plurality of alternating protrusions and recesses positioned within the shell housing. The proximal end of the at least one steering tendon is connected to the steering controller. The steering controller is adapted to translate between a locked position and a free position. In the locked position, at least one of the steering controller protrusions and recesses is engaged with at least one of the shell housing protrusions or recesses. In the free position, the steering controller protrusions and recesses are disengaged from the shell housing protrusions and recesses and the steering controller is manipulable to adjust tension to the least one steering tendon.

In a detailed aspect, the plurality of protrusions and recesses form teeth. In a more detailed aspect, the steering controller includes a rotatable steering knob that includes a shaft portion located internal the shell housing and a controller portion located external the shell housing. The steering controller further includes a rotatable steering disk that carries the steering controller protrusions and recesses. The steering disk is located internal the shell housing and is attached to the shaft portion of the knob. The steering controller also includes a spring for biasing the steering disk toward the shell housing protrusions and recesses such that the steering controller protrusions and recesses engage at least one of the shell housing protrusions and recesses. In an even more detailed aspect, the steering controller protrusions and recesses are located along the perimeter of the steering disk. In another detailed facet, the force with which the spring biases the steering disk in the locked position is adjustable. In another detailed aspect, the steering controller further includes a spacer that is located internal the shell housing and is attached to the shaft portion of the knob. In a more detailed aspect, the spring biases the steering disk via the spacer. In an even more detailed aspect, the spring includes any one of a compression spring, tension spring, leaf spring and Belleville spring washers, and the biasing force is adjustable via a screw. In a further detailed aspect the steering disk is disengaged from the shell housing via the application of force upon the steering knob that opposes the biasing force.

In a third aspect, the invention relates to a catheter that includes a catheter shaft that has a proximal region and a distal-end region and at least one steering tendon. The steering tendon has a distal end that is attached to the shaft distal-end region and a proximal end that exits the proximal end of the shaft. The catheter also includes a shell housing having the proximal end of the shaft attached thereto. The shell housing includes a plurality of alternating protrusions and recesses positioned within the shell housing. The catheter also includes a steering controller that is carried by the shell housing. The steering controller has a plurality of alternating protrusions and recesses that are positioned within the shell housing. The proximal end of the at least one steering tendon is connected to the steering controller. The steering controller is adapted to translate between a locked position and a free position. In the locked position, at least one of the steering controller protrusions or recesses is engaged with at least one of the housing protrusions or recesses. In the free position, none of the steering controller protrusions or recesses is engaged with any of the housing protrusions or recesses and the steering controller is manipulable to apply or release tension to the steering tendon.

In a detailed aspect of the invention, there is at least one electrode positioned at the distal-end region of the shaft. In a further aspect of the invention, the steering controller includes a rotatable steering knob that includes a shaft portion located internal the shell housing and a controller portion located external the shell housing. The steering controller farther includes a rotatable steering disk located internal the shell housing that is attached to the shaft portion of the knob. The steering disk carries the steering controller protrusions and recesses. The steering controller also includes a spacer located internal the shell housing that is also attached to the shaft portion of the knob, and a compression spring that biases the steering disk, via the spacer, toward the shell housing protrusion and recesses such that the steering controller protrusion and recesses engage at least one of the shell housing protrusion and recesses. In a more detailed aspect, the force with which the compression spring biases the steering disk in the locked position via the spacer is adjustable.

In a fourth aspect, the invention relates to a method of steering a catheter shaft that has at least one steering tendon by using a handle that includes a shell housing with a plurality of alternating protrusions and recesses and a rotatable steering controller that also has a plurality of alternating protrusions and recesses. The housing protrusions and recesses are normally engaged with the controller protrusions and recesses by a biasing force. The method includes the step of disengaging the controller protrusions and recesses from the housing protrusions and recesses. The method also includes the step of rotating the controller to pull on the at least one steering tendon and thereby deflect the profile of the shaft. Also included is the step of reengaging the controller protrusions and recesses with the housing protrusions and recesses.

In a detailed aspect of the invention, the step of disengaging the controller protrusions and recesses from the housing protrusions and recesses includes opposing the biasing force with a force greater than the biasing force. In another aspect, the step of reengaging the controller protrusions and recesses with the housing protrusions and recesses comprises opposing the biasing force with a force less than the biasing force.

These and other aspects and advantages of the invention will become apparent from the following detailed description and the accompanying drawings, which illustrate by way of example the features of the invention.

BRIEF DESCRIPTION OF THE DRAWINGS

FIG. 2 is a plan view depicting the disk housing shell portion of the catheter handle of FIG. 1;

FIG. 3 is a plan view depicting the spacer housing shell portion of the catheter handle of FIG. 1;

FIG. 4 is an exploded isometric view of the handle of FIG. 1 depicting major components of the catheter handle including the handle shell and the steering controller;

FIG. 5 is a section view of the steering controller taken along the line 5—5 in FIG. 1;

DETAILED DESCRIPTION OF THE PREFERRED EMBODIMENTS

Figure 1:
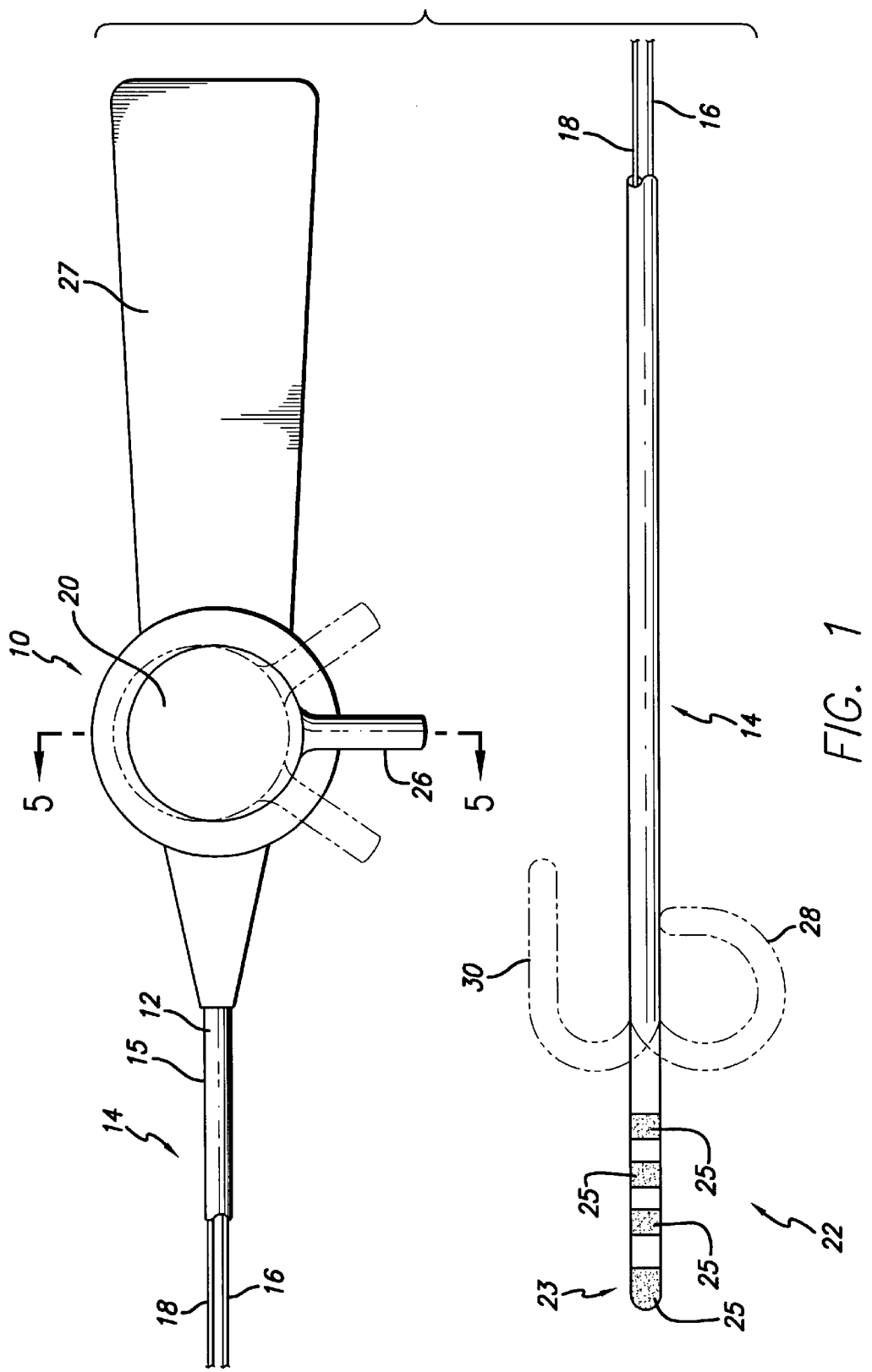
FIG. 1 is a plan view of a catheter handle and catheter configured in accordance with the invention and depicting major components of the catheter handle and catheter including a handle shell, a steering controller, and a catheter shaft.

Referring now to the drawings, in which like reference numerals are used to designate like or corresponding elements among the several figures, in FIG. 1 there is shown a catheter handle 10 for a steerable catheter incorporating aspects of the present invention. The catheter handle 10 attaches to a proximal end 12 of a catheter shaft 14. The catheter shaft comprises a catheter sheath 16, a first steering tendon 18 and a second steering tendon 20. The first steering tendon 18 and the second steering tendon 20 exit from the proximal end of the catheter sheath 16 and enter the catheter handle 10. Within the catheter handle 10, the first 18 and second 20 steering tendons attach to a steering controller 22. The distal ends of the steering tendons 18, 20 are attached to a distal-end region 24 of the catheter, in a manner such as that disclosed in co-pending patent application having Ser. No. 09/848,087, entitled "Dual-Profile Steerable Catheter with Shaft Support System for Resisting Axial Compressive Loads," that was filed on May 2, 2001, which is assigned to the assignee of the present invention and is hereby incorporated by reference.

With continued reference to FIG. 1, the distal-end region 24 of the catheter shaft 14 also includes an energy transfer device 26. In one configuration, the energy transfer device 26 includes a tip electrode 28 for applying ablation energy to a biological site. Proximal from the tip electrode 28 is a plurality of band electrodes 30 arranged in a substantially linear array along the distal-end region 24 of the sheath 16. The energy transfer device 26 includes individual feed wires (not shown) running from the catheter handle 10 to each band electrode 30. The feed wires are attached to the band electrodes 30, such as by welding. The energy transfer device 26 also includes a pair of thermocouple wires (not shown) running from the catheter handle 10 through the catheter sheath 16 to the tip electrode 28. The thermocouple wires are attached to the tip electrode 28, such as by soldering. One of the thermocouple wires also functions as a drive wire to transmit ablation energy to the tip electrode 28.

With further reference to FIG. 1, the profile of the distal-end region 24 of the catheter shaft 14 can be adjustably deflected by rotating the steering controller 22. A knob 32 portion of the steering controller 22 resides partially outside the handle's shell 34. The steering controller 22 can be rotated by rotating the knob 32 either in a first direction (clockwise) or in a second direction (counterclockwise). Rotating the knob 32 clockwise from a neutral position causes one of the steering tendons 18,20 to translate axially in the proximal direction, thus creating a first changed profile 36 of the distal-end region 24 of the catheter shaft 14. Similarly, rotating the knob 32 counterclockwise from the neutral position causes the other steering tendon 18, 20 to translate axially in the proximal direction, thus creating a second changed profile 38 of the distal-end region 24 of the catheter shaft 14. Although FIG. 1 depicts the handle being used with a dual-profile catheter with two steering tendons 18, 20, the handle 10 is also functional for single-profile catheters with a single steering tendon.

The shell 34 of the handle 10 comprises a disk housing shell 40 (FIG. 2) and a spacer housing shell 42 (FIG. 3). Referring to FIG. 2 which depicts the internal configuration of the disk housing shell 40, the distal end 44 of the disk housing shell includes a channel 46 for receiving and housing the catheter shaft 14 (FIG. 1). Proximal the channel 46 is a pocket 48 that receives a cylindrical adapter (not shown in FIG. 2). As will be discussed in more detail below, the catheter shaft 14 is adhesively bonded into a hole in the adapter, and the adapter is adhesively bonded into the pocket 48, thus holding the catheter shaft in place relative to the handle 10. Proximal the pocket 48 is a steering disk housing 50. One side along the inner perimeter of the steering disk housing 50 includes a plurality of alternating protrusions and recesses 52. As will be discussed further below, the alternating protrusions and recesses 52 in the steering disk housing 50 mate with a plurality of alternating protrusions and recesses on a steering disk (not shown in FIG. 2). The steering disk housing 50 also includes a lateral slot 54 that receives and controls the direction of translation of a steering controller shaft (not shown in FIG. 2). Proximal the steering disk housing 50 is a handgrip portion 56 of the disk housing shell 40. The proximal-most portion of the handgrip portion 56 includes a channel 58 for holding an electrical connector 59 (FIG. 4).

Referring to FIG. 3 which depicts the internal configuration of the spacer housing shell 42, the distal end 60 of the spacer housing shell includes a channel 62 for receiving and housing the catheter shaft 14 (FIG. 1). Proximal the channel 62 is a pocket 64 that receives a cylindrical adapter (not shown in FIG. 3). Upon assembly of the handle shell 34, the channel 62 complements the channel 46 in the disk housing shell 40 (FIG. 2) to form a lumen to house the proximal portion 12 of the catheter shaft 14 (FIG. 1), and the pocket 64 complements the pocket 48 (FIG. 2) in the disk housing shell to form a single pocket for housing the cylindrical adapter. Proximal the pocket 64 is a spacer housing 66. Within the spacer housing 66 is a rectangular pocket 68 for containing a spacer (not shown in FIG. 3); the spacer will be described in more detail below. The rectangular pocket 68 permits the spacer to translate laterally, but restrains the spacer from translating longitudinally. The spacer housing 66 also includes a lateral slot 70 that is aligned with the lateral slot 54 (FIG. 2) in the steering disk housing 50 to receive and control the direction of translation of the steering controller shaft (not shown in FIG. 3). Proximal the spacer housing 66 is a handgrip portion 72 of the spacer housing shell 42. The handgrip portion 72 of the spacer housing shell 42 mates with the handgrip portion 56 (FIG. 2) of the disk housing shell 40 to form a complete handgrip 74 (see FIG. 1). The proximal-most portion of the handgrip portion 72 includes a channel 75 that complements the channel 58 (FIG. 2) in the disk housing shell 40 to form an aperture for holding an electric connector 59 (FIG. 4).

With reference to FIG. 4, the disk housing shell 40 and spacer housing shell 42 are mated and joined to each other at various attachment points after installation of the interior components of the handle. One of the attachment points is at the location of the cylindrical-shaped adapter 114. The adapter 114 fits into the matching pockets 48 (FIG. 2), 64 (FIG. 3) within the distal section 44, 60 of the disk housing shell 40 and the spacer housing shell 42 respectively. The adapter 114 is adhesively bonded to the matching pockets 48 (FIG. 2), 64 (FIG. 3), such as with cyanoacrylate, thereby joining the disk housing shell 40 and the spacer housing shell 42 at that attachment point. The disk housing shell 40 and the spacer housing shell 42 are also joined at at least one other attachment point with a screw 77. In the embodiment of FIG. 4, two screws 77 are shown.

With further reference to FIG. 4 and reference to FIG. 5, the steering controller 22 comprises the knob 32, a steering disk 76, a spacer 78, a compression spring 80, and a setscrew 82. The knob 32 further comprises a knob disk hub 84, a knob disk shaft 86, and a knob connecting bar 88. The knob disk hub 84 and the knob disk shaft 86 each comprise a disk portion 90, 92 and a shaft portion 94, 96. The shaft portions 94, 96 protrude perpendicularly from the center of their respective disk portions 90, 92. The shaft portion 94 of the knob disk hub 84 is inserted into the lateral slot 54 in the disk housing shell 40 and the shaft portion 96 of the knob disk shaft 86 is inserted into the lateral slot 70 in the spacer housing shell 42. O-rings 98 are placed within grooves 100 in the knob disk hub 84 and the knob disk shaft 86 to provide standoff between the steering knob 32 and the handle shell 34 so that the steering knob does not rub against the handle shell. Both O-rings 98 are lubricated with silicone oil, such as Dow™ 360 or equivalent, to minimize drag. Within the handle 10, the shaft portion 94 of the knob disk hub 84 mates with and is adhesively bonded, such as by gluing, to the shaft portion 96 of the knob disk shaft 86, thus forming a single shaft 102. The knob connecting bar 88 is also adhesively bonded, such as by gluing, between radial protrusions 104, 106 on the knob disk hub 84 and the knob disk shaft 86 to ensure that the knob disk shaft and the knob disk hub move synchronously.

With continued reference to FIGS. 4 and 5, a center hole 108 on the steering disk 76 is keyed to the shaft portion 102 of the knob 32 so that turning the knob causes the steering disk to rotate. The spacer 78 also has a hole 110 that mates with the shaft 102 of the knob 32. The hole 110 in the spacer 78 is round and provides a loose fit with the shaft 102. The spacer 78 is a mostly rectangular-shaped block that fits within the rectangular pocket 68 in the spacer housing shell 42. The spacer 78 is normally biased to one side of the pocket by the compression spring 80. The compression spring 80 fits between the setscrew 82 within the wall of the spacer housing shell 42 and an aperture 112 in an end of the spacer 78. The force exerted by the compression spring 80 can be adjusted via the setscrew 82.

Although in a preferred embodiment the spacer 78 is biased by the compression spring 80, other means maybe utilized to accomplish the same result. For instance, the spacer 78 can be biased by tension springs, leaf springs, or numerous other types of springs. The spacer 78 can also be biased by hydraulic pressure, pneumatic pressure, compressible materials, elastic materials, magnetic forces, or by any equivalent means. Similarly, the force exerted by the compression spring 80 can be adjusted by means other than the setscrew 82 to accomplish the same result. As an example, other screw types or threaded devices could be used. The force can also be adjusted by a ratchet system, shims, wedges, hydraulic pressure, pneumatic pressure, or by any equivalent means.

Figure 6A:
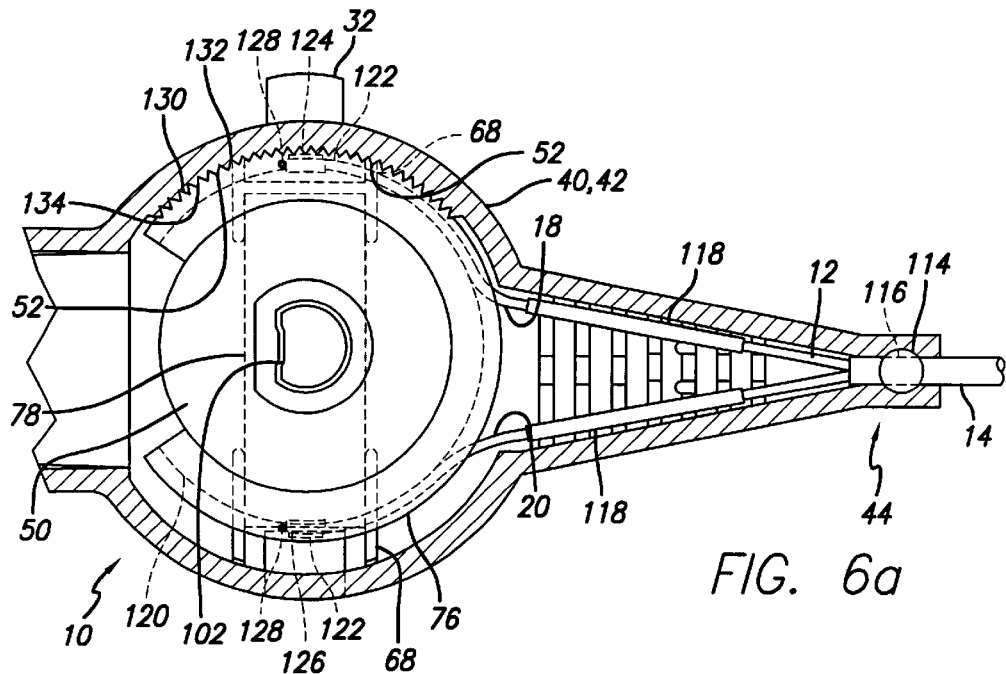
FIG. 6a is a section view of the steering controller taken along the line 6a—6a in FIG. 5 depicting the steering controller engaged with the handle shell in the locked position.
Figure 6B:
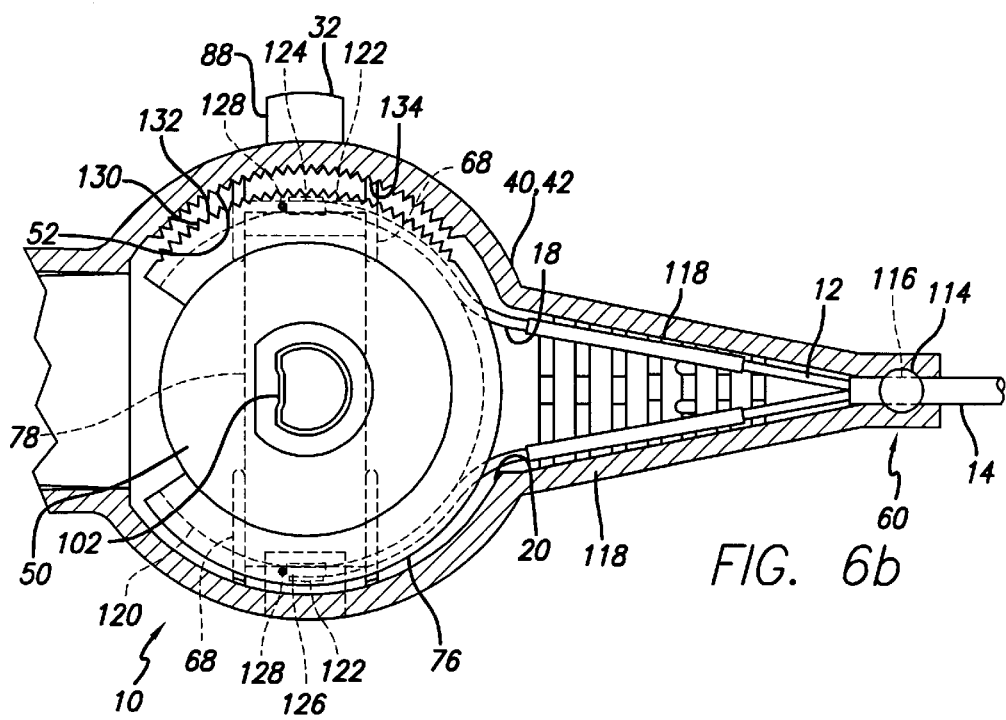
FIG. 6b is a section view of the steering controller taken along the line 6b—6b in FIG. 5 depicting the steering controller disengaged from the handle shell in the free position.

Referring to FIGS. 6a and 6b, the cylindrical-shaped adapter 114 has a hole 116 (see FIG. 4) running laterally through it. To attach the catheter shaft 14 to the handle 10, the proximal end 12 of the catheter shaft is inserted into the hole 116 and is attached to the hole such as by adhesive bonding. As mentioned previously, the adapter 114 is subsequently attached, such as by adhesive bonding, to the matching pockets 48 (FIG. 2), 64 (FIG. 3).

With continued reference to FIGS. 6a and 6b, the first 18 and second 20 steering tendons exit the proximal end 12 of the catheter shaft 14 and enter the handle 10. Within the handle 10, the steering tendons 18,20 are routed through guide tubes 118 that comprise a low-friction material, such as polyimide. From the guide tubes 118, each of the steering tendons 18, 20 wraps partially around a hub 120 of the steering disk 76 and feeds through a notched portion 122 of the hub. At the proximal end 124, 126 of each steering tendon 18, 20 is a tendon stop 128. As the steering disk 76 is rotated, the notched portion 122 pulls on the tendon stop 128 of one of the steering tendons 18,20 and causes that steering tendon to axially translate in the proximal direction, thereby causing the catheter shaft 14 to steer.

With further reference to FIGS. 6a and 6b, a perimeter of the steering disk 76 includes a plurality of alternating protrusions and recesses 130 that mate with the plurality of alternating protrusions and recesses 52 on the inside surface of the steering disk housing 50 (FIG. 6a). The resolution of locking locations is controlled by the sizes and spacing of the protrusions and recesses 52, 130. The number of locking positions increases as the number of protrusions and recesses 52, 130 increases. The finer the protrusions and recesses 52, 130 are, the more that can be disposed in any given arc. This allows greater resolution. However, they cannot be so fine that a force on the distal end of the catheter translated to the steering controller 22 by a tendon 18, 20 can pull the steering disk 76 out of its locked position. In one configuration, the alternating protrusions and recesses 130 on the steering disk 76 and the alternating protrusions and recesses 52 in the steering disk housing 50 form teeth 132, 134. The teeth 132 on the steering disk 76 can be disengaged (FIG. 6b) from the teeth 134 in the steering disk housing 50 by pushing the knob connecting bar 88 radially towards the center of the handle 10 with a force greater than the biasing force of the spring 80. By pushing the knob connecting bar 88 radially towards the center of the handle 10 with a force greater than the biasing force of the spring 80 (FIG. 5), the shaft 102 translates within the slots 54, 70 in the spacer housing 66 and the steering disk housing 50. As the steering knob 32 translates, the shaft 102 causes the steering disk 76 and the spacer 78 to translate with it, thereby causing the teeth 132 in the steering disk to disengage from the steering disk housing 50 and causing further compression of the compression spring 80 (FIG. 5). With the steering disk 76 disengaged (FIG. 6b), the knob connecting bar 88 can be rotated clockwise or counterclockwise about the shaft 102, thus rotating the steering disk and pulling one of the steering tendons 18, 20 to cause the profile of the distal-end region 24 (FIG. 1) of the catheter shaft 14 to change.

Although in a preferred embodiment the steering disk 76 mates with the steering disk housing 50 through a plurality of alternating protrusions and recesses 52, 130 on the steering disk and on the steering disk housing, other means may be utilized to accomplish the same result. For instance, an array of protrusions can be disposed on the steering disk 76 for mating with an array of apertures disposed on the steering disk housing 50, or vice versa. Alternatively, the same result can be achieved with a single protrusion on the steering disk 76 that mates with any of a series of apertures on the steering disk housing 50, or vice versa, or by any equivalent means. Other possible methods for accomplishing the same result include the use of surface textures including sandpaper, coarse fabric, a file, or other suitable coarse materials. High friction materials such as low durometer "sticky" rubbers, such as chlorbutyl rubber, also produce satisfactory results. In a preferred embodiment the teeth 132, 134 formed from the alternating protrusions and recesses 52, 130 comprise a triangular shape. The teeth 132, 134 can also comprise other shapes such as square, rectangular, semicircular, rounded-tip triangular, rounded-tip rectangular, or any other suitable shape. However, the triangular pointed shape permits the teeth 132, 134 to self-guide their engagement with mating teeth.

While the mating portions have thus far been described as being located within the shell 34 of the handle 10, the handle may be configured such that the mating portions are located outside of the shell. For example, the exterior surface of the disk housing shell 40 may be formed to include alternating protrusions and recesses. In such a configuration, the steering controller 22 includes an additional component (not shown) exterior the shell 34 and opposite its knob 32 that carries complementary alternating protrusions and recesses that are normally engaged with those on the disk housing shell 40. Application of force on the knob 32 toward the additional component disengages the protrusions and recesses and allows for rotation of the steering controller 22.

With additional reference to FIGS. 6a and 6b, when the desired profile 36, 38 (FIG. 1) of the distal-end region 24 of the catheter shaft 14 has been reached, the applied force on the knob connecting bar 88 is reduced to an amount less than the biasing force of the compression spring 80 (FIG. 5). Reducing the applied force on the knob connecting bar 88 allows the compression spring 80 (FIG. 5) to decompress and biases the spacer 78 back to the opposite side of the rectangular pocket 68 (FIG. 5). As the compression spring 80 (FIG. 5) biases the spacer 78, the spacer causes the shaft 102 to translate with it, which in turn causes the steering disk 76 to translate and to reengage with the teeth 134 in the steering disk housing 50. With the force removed from the knob connecting bar 88 and the compression spring 80 biasing the spacer 78, the steering disk 76 is locked in place and retains the changed profile 36, 38 (FIG. 1) of the distal-end 24 of the catheter shaft 14. Thus, because of its ability to automatically hold the catheter's distal profile 36, 38 (FIG. 1) when released, the handle 10 does not require a second operation to lock the desired profile in place.

In operation, the set of teeth 132 on the steering disk 76 is normally engaged with the set of teeth 134 on the inside surface of the steering disk housing 50. To change the profile of the distal-end region 24 (FIG. 1) of the catheter shaft 14 and lock it in place, the operator first disengages the teeth 132 on the steering disk 76 from the teeth 134 on the inside surface of the steering disk housing 50 (see FIGS. 6a and 6b). This step is accomplished by the operator applying a force to the knob connecting bar 88 of the steering controller 22 that is greater than the biasing force of the compression spring 80 (FIG. 5). With the teeth 132 (FIG. 6b) on the steering disk 76 disengaged from the teeth 134 on the inside surface of the steering disk housing 50, the operator can rotate the controller 22 to affect the profile of the distal-end region 24 of the shaft 14 (FIG. 1). Alternatively, depending on the size and shape of the teeth 132, 134, the teeth do not need to be disengaged before rotating the steering controller 22, or only require partial disengagement. Rather, with such sized and shaped teeth 132, 134, rotation of the steering controller 22 can occur by pushing harder on the knob connecting bar 88 in the clockwise or counterclockwise direction. Such manipulation of the steering controller 22 causes the steering controller to operate similar to a ratchet, thus causing an obvious sound during rotation. Upon obtaining a desired profile 36, 38 (FIG. 1) of the distal end region 24 of the shaft 14, the teeth 132 (FIG. 6a) on the steering disk 76 are reengaged with the teeth 134 on the inside surface of the steering disk housing 50 by the operator applying a force less than the biasing force of the compression spring 80 to the steering controller 22.

Thus, the deflection of the distal-end region 24 of the catheter shaft 14 and locking the steering controller 22 in the selected position can be accomplished with a single hand. For example, referring to FIG. 1, an operator can hold the handle 10 in his or her right hand with the thumb extended and in contact with the connecting bar 88. The operator moves his thumb inward towards his palm thereby disengaging the locking teeth 132, 134 (FIGS. 6a and 6b) from each other. When the locking teeth 132, 134 have disengaged, the operator then moves the connecting bar 88 in the clockwise or counterclockwise direction with his same thumb until the desired deflection 36, 38 of the distal-end region 24 of the catheter shaft 14 is obtained. The operator may then slowly release his thumb from the connecting bar 88 to allow the spring to drive the locking teeth 132 on the steering disk 76 into the locking teeth 134 on the disk housing shell 40. Thus, one-handed operation is easily accomplished.

It will be apparent from the foregoing that, while particular forms of the invention have been illustrated and described, various modifications can be made without departing from the spirit and scope of the invention.

What is claimed is:

1. A self-locking handle for steering a catheter shaft having a proximal region and a distal-end region and at least one steering tendon having a distal end attached to the shaft distal-end region and a proximal end exiling the shaft proximal end, said handle comprising:

a shell housing having the proximal end of the catheter shaft attached thereto;

a steering controller carried by the shell housing and having the proximal end of the at least one steering tendon connected thereto, the steeling controller adapted for movement to apply tension to the at least one steering tendon;

a self-locking means for retaining the steering controller in a locked position to prevent movement thereof; and means for moving the steering controller from the locked position to a free position wherein the steering controller is manipulable to adjust tension to the at least one steering tendon.

2. The self-locking handle of claim 1 wherein the steering controller comprises:

a rotatable steering knob comprising a shaft portion located internal the shell housing and a controller portion located external the shell housing; and a rotatable steering disk located internal the shell housing and attached to the shaft portion of the knob.

3. The self-locking handle of claim 1 wherein the retaining means comprise;

first mating means carried by the shell housing;

second mating means carried by the steering controller; and means for biasing the second mating means against the first mating means such that the first and second mating means engage.

4. The handle of claim 3 wherein:

the first mating means comprises a plurality of alternating protrusions and recesses; and the second mating means comprises a plurality of alternating protrusions and recesses.

5. The handle of claim 4 wherein the pluralities of alternating protrusions and recesses form teeth.

6. The handle of claim 3 further comprising means for adjusting the force with which the biasing means biases the second mating means against the first mating means.

7. The handle of claim 6 wherein the adjusting means comprises a screw.

8. The handle of claim 3 wherein the biasing means comprises any one of a compression spring, tension spring, leaf spring and Belleville spring washers.

9. The handle of chum 3 wherein the means for moving the steering controller comprise means for receiving force sufficient to disengage the second mating means from the first mating means.

10. The handle of claim 9 wherein the steering controller comprises a rotatable steering knob including a shaft portion located internal the shell housing and a controller portion located external the shell housing and the force-receiving means comprise the controller portion.

11. A handle for steering a catheter shaft having a proximal region and a distal-end region and at least one steering tendon having a distal end attached to the shaft distal-end region and a proximal end exiting the shaft proximal end, said handle comprising:
- a shell housing attached to the proximal end of the catheter shaft and having a plurality of alternating protrusions and recesses positioned within the shell housing; and
- a steering controller carried by the shell housing and having a plurality of alternating protrusions and recesses positioned within the shell housing, and having the proximal end of the at feast one steering tendon connected thereto;
- wherein the steering controller is adapted to translate between a locked position wherein at least one of the steering controller protrusions and recesses is engaged with at least one of the shell housing protrusions or recesses, and a free position wherein the steering controller protrusions and recesses are disengaged from the shell housing protrusions and recesses and the steering controller is manipulable to adjust tension to the at least one steering tendon.

12. The handle of claim 11 wherein the plurality of protrusions and recesses form teeth.

13. The handle of claim 11 wherein the steering controller comprises:
- a rotatable Steering knob comprising a shaft portion located internal the shell housing and a controller portion located external the shell housing;
- a rotatable steering disk located internal the shell housing and attached to the shaft portion of the knob, the steering disk carrying the steering controller protrusions and recesses; and
- a biasing device coupled to the steering disk to urge the steering disk protrusions and recesses into engagement with the shell housing protrusions and recesses.

14. The handle of claim 13 wherein the steering controller protrusions and recesses are located along the perimeter of the steering disk.

15. The handle of claim 13 wherein the biasing device comprises a spring.

16. The handle of claim 15 wherein the force with which the spring biases the steering disk is adjustable.

17. The handle of claim 16 further comprising a screw in contact with the spring wherein the position of the screw controls the amount of biasing force exerted by the spring.

18. The handle of claim 15 wherein the spring comprises any one of a compression spring, tension spring, leaf spring and Belleville spring washers.

19. The handle of claim 13 wherein the steering disk is disengaged from the shell housing via the application of a force upon the steering knob that opposes the biasing force.

20. A catheter comprising:
- a catheter shaft having a proximal region and a distal-end region, and at least one steering tendon having a distal end attached to the shaft distal-end region and a proximal end exiting the shaft proximal end;
- a shell housing having the proximal end of the shaft attached thereto and a plurality of alternating protrusions and recesses positioned within the shell housing; and
- a steering controller carried by the shell housing and having a plurality of alternating protrusions and recesses positioned within the shell housing and having the proximal end of the at least one steering tendon connected thereto;
- wherein the steering controller is adapted to translate between a locked position wherein at least one of the steering controller protrusions or recesses is engaged with at least one of the housing protrusions or recesses, and a free position wherein none of the steering controller protrusions or recesses is engaged with any of the housing protrusions or recesses and the steering controller is manipulable to apply or release tension to the steering tendon.

21. The catheter of claim 20 further comprising at least one electrode positioned in the distal-end region of the shaft.

22. The catheter of claim 20 wherein the steering controller comprises:
- a rotatable steering knob comprising a shaft portion located internal the shell housing and a controller portion located external the shell housing;
- a rotatable steering disk located internal the shell housing and attached to the shaft portion of the knob, the steering disk carrying the steering controller protrusions and recesses;
- a spacer located internal the shell housing and attached to the shaft portion of the knob; and
- a compression spring for biasing the steering disk via the spacer, toward the shell housing protrusions and recesses such that the steering controller protrusion and recesses engage at least one of the shell housing protrusion and recesses.

23. The catheter of claim 22 wherein the force with which the compression spring biases the steering disk in the locked position via the spacer is adjustable.

24. The catheter of claim 20 wherein the plurality of alternating protrusions and recesses form teeth.

25. A method of steering a catheter shaft having at least one steering tendon using a handle having a shell housing with a plurality of alternating protrusions and recesses, and a rotatable steering controller with a plurality of alternating protrusions and recesses, wherein the housing protrusions and recesses arc normally engaged with the controller protrusions and recesses by a biasing force, said method comprising:
- disengaging the controller protrusions and recesses from the housing protrusions and recesses;
- rotating the controller to pull on the at least one steering tendon and thereby deflect the profile of the shaft; and
- reengaging the controller protrusions and recesses with the housing protrusions and recesses.

26. The method of claim 25 wherein the step of disengaging the controller protrusions and recesses from the housing protrusions and recesses comprises opposing the biasing force with a force greater than the biasing force.

27. The method of claim 25 wherein the step of reengaging the controller protrusions and recesses with the housing protrusions and recesses comprises opposing the biasing force with a force less than the biasing force.

28. A self-locking handle for steering a catheter shaft having a proximal region and a distal-end region and at least one steering tendon having a distal end attached to the shaft distal-end region and a proximal end exiting the shaft proximal end, said handle comprising:
- a steering controller having the proximal end of the at feast one steering tendon connected thereto, the steering controller adapted for movement to apply tension to the at least one steering tendon; and a locking device connected to the steering controller that automatically lacks the steering controller into a selected position;

wherein the steering controller is manipulable between the locked position and a free position; and wherein in the free position the steering controller is manipulable to adjust tension to the at least one steering tendon.

* * * * *